US007053175B1

(12) United States Patent
Chenebaux et al.

(10) Patent No.: US 7,053,175 B1
(45) Date of Patent: May 30, 2006

(54) SYNTHETIC PEPTIDES USEFUL IN BIOLOGICAL ASSAYS FOR DETECTING INFECTIONS CAUSED BY GROUP O HIV-1 VIRUSES

(75) Inventors: Denis Marie Bernárd Chenebaux, Versailles (FR); Jean-Francois Hubert Delagneau, La Celle Saint Cloud (FR); Stephane Jean Xavier Gadelle, Bievres (FR); François Yves Rieunier, Fontenay le Fleury (FR)

(73) Assignee: Bio-Rad Pasteur, Marnes la Coquette (FR)

( * ) Notice: Subject to any disclaimer, the term of this patent is extended or adjusted under 35 U.S.C. 154(b) by 0 days.

(21) Appl. No.: 09/147,362

(22) PCT Filed: Apr. 6, 1998

(86) PCT No.: PCT/FR98/00691

§ 371 (c)(1),
(2), (4) Date: Mar. 12, 1999

(87) PCT Pub. No.: WO98/45323

PCT Pub. Date: Oct. 15, 1998

(30) Foreign Application Priority Data

Apr. 9, 1997 (FR) .......................................... 97 04356
Feb. 24, 1998 (FR) .......................................... 98 02212

(51) Int. Cl.
*A61K 38/00* (2006.01)

(52) U.S. Cl. ....................... 530/300; 530/324; 530/325; 530/326; 424/188.1; 424/208.1

(58) Field of Classification Search ................. 530/300, 530/324–327; 424/188.1, 208.1
See application file for complete search history.

(56) References Cited

U.S. PATENT DOCUMENTS 5,830,634 A * 11/1998 Brust et al. .................... 435/5

FOREIGN PATENT DOCUMENTS

| | | | |
|---|---|---|---|
| WO | WO95/32293 | | 11/1995 |
| WO | WO96/12809 | | 5/1996 |
| WO | WO 96/12809 | * | 5/1996 |
| WO | WO96/27012 | | 9/1996 |
| WO | WO96/27013 | | 9/1996 |
| WO | WO 96 27912 | | 9/1996 |

OTHER PUBLICATIONS

Alexander, H., et al., 1992, "Altering the antigenicity of proteins", Proc. Natl. Acad. Sci. USA 89:3352–3356.*
Schoofs, P., et al., 1988, "Epitopes of an influenza viral peptide recognized by antibody at single amino acid resolution", J. Immunol. 140:611–616.*

* cited by examiner

*Primary Examiner*—Jeffrey S. Parkin
(74) *Attorney, Agent, or Firm*—Jacobson Holman PLLC

(57) ABSTRACT

Synthetic peptides of the monomer type with 13 to 33 amino acids, in linear form or in a form cyclized by means of inter-cysteine disulphide bridges, have the general formula (I):

$$\Delta\text{-Z-TrpGlyCys-}\Theta\text{-CysTyrThrSer-}\Omega \qquad (I)$$

wherein Δ is a biotinyl radical, a biocytinyl radical, a hydrogen atom, an acetyl ($CH_3CO$—) radical, an aliphatic chain which may contain one or two thiol, an aldehyde functional group, or an amine functional group, Z represents peptide sequence $-\Xi_1$-Ser-$\Xi_2$-, $-\Xi_1$-Gln-$\Xi_2$-, or $-\Xi_1$-Asn-$\Xi_2$-, wherein $-\Xi_1$ represents a peptide sequence of 0 to 9 amino acids and $-\Xi_2$ represents a peptide sequence of 0 to 5 amino acids, Θ is -Arg Gly Arg Leu Ile-(SEQ ID NO: 15), -Arg Gly Arg Leu Val-(SEQ ID NO: 16), -Arg Gly Lys Leu Ile- (SEQ ID NO: 17), -Arg Gly Lys Leu Val-(SEQ ID NO: 18), -Lys Gly Arg Leu Ile-(SEQ ID NO: 19), or -Lys Gly Arg Leu Val-(SEQ ID NO: 20), Ω, attached to the —CO— group of serine, is a hydroxyl (—OH) radical, an amino (—$NH_2$) radical, an alkoxy radical having 1 to 6 carbon atoms, a peptide sequence of formula Val-Σ-Ψ wherein Σ represents a sequence of formula -($AA_1$)-Trp Asn-($AA_2$)-($AA_3$) wherein ($AA_1$) represents an amino acid different from lysine, ($AA_2$) represents an amino acid, and ($AA_3$) is serine or a threonine residue, and Ψ, attached to the —CO— residue of the free $AA_3$ amino acid, is OH, $NH_2$, or an alkoxy radical having from 1 to 6 carbon atoms, and a peptide sequence of formula -Val-Ψ wherein Ψ, attached to the —CO— residue of valine, is OH, $NH_2$, or an alkoxy radical having from 1 to 6 carbon atoms.

11 Claims, No Drawings

SYNTHETIC PEPTIDES USEFUL IN BIOLOGICAL ASSAYS FOR DETECTING INFECTIONS CAUSED BY GROUP O HIV-1 VIRUSES

The invention relates to synthetic peptides which can be used in biological tests for the detection of infections due to the group O HIV-1 viruses, to the method for preparing them, to compositions and kits containing such peptides and to the biological tests using such peptides.

Group O HIV-1 retroviruses are known in the prior art. Patent EP 0,345,375 and patent application EP 0,657,532 describe the ANT 70 and ANT 70 NA isolates isolated from Cameroonian patients. These documents describe more precisely antigens and antigenic compositions containing lysates or proteins of these isolates, the nucleic acids corresponding to the genomic RNA, hybridization method using these nucleic acids, methods of producing the isolates indicated above as well as methods of preparing p12, p16, p25, gp41 and gp120 proteins of these retroviruses.

Application EP 0,591,914 describes the MVP 5180/91 isolate. This isolate, characterized by Western blotting, exhibits, like the previous isolate, differences in relation to the HIV-1 retrovirus isolates which have been known for a long time. Application EP 0,591,914 describes precisely the DNA sequence of the MVP 5180/91 isolate and indicates precisely the location of the gag, pol and env genes. Application EP 0,591,914 further describes synthetic peptides of the V3 loop as well as the immunodominant region (gp41). They are useful for biological tests, in particular for the in vitro detection of group O HIV-1 antibodies.

Application EP 0,673,948 describes synthetic or recombinant peptides consisting of 15 to 50 amino acids (AA) and comprising the sequence -VWGIRQLRARLQALETLIQNQQRLNLWGXKGKLIXYTSVKWNTSWSGR-(SEQ ID NO:22) in which X represents either a cysteine residue, or a serine residue. These peptides are useful in the diagnostic field for the detection of infections due to certain group O HIV-1 retrovirus isolates.

Application EP 0,727,483 is also known which describes the MVP 2901/94 isolate which also forms part of the retroviruses belonging to the group O HIV-1 family. This application describes certain antigens having well-determined peptide sequences. These peptide sequences correspond to part of the sequence of gp120 and part of gp41 (immunodominant region) of the MVP 2901/94 isolate.

Application WO 96/12809 describes two new isolates belonging to the group O HIV-1 family. They are the VAU and DUR isolates. This application describes certain peptide sequences derived from the two viruses cited above, which are useful for the detection of antibodies recognizing the HIV-1 VAU or DUR peptide sequences.

Application WO 96/32293 describes two antigens derived from the sequence of the ANT 70 isolate. They are the antigen called MDL061 and the antigen MDL056, of the immunodominant region of gp41. According to this invention, to detect 100% of the samples of a limited collection of sera from patients infected with the group O HIV-1 virus, it is necessary to use compositions containing these two peptides, since each isolated peptide does not allow, on its own, satisfactory results to be obtained.

Indeed, it is practically impossible, in the light of the genetic variability shown by the isolates of the group O virus, to guarantee serological screening of individuals infected by the use of antigens derived from the same and sole isolate. This means that it is not possible to obtain reagents which guarantee 100% sensitivity. The 0 group thus raises, for the first time, a major problem; it is the inability of certain serological reagents to recognize individuals infected with particularly divergent groups or subtypes. This is precisely the case for the group O HIV-1 viruses.

Application WO 96/40763 also stresses the great divergence of the O group. This application describes peptides which incorporate, into a natural HIV-1 type B sequence, a few minor modifications (replacement of one or two amino acids). According to this application, these hybrid peptides are capable of reacting with anti-group O antibodies.

Application WO 96/27013 describes a series of new group O HIV-1 viruses designated BCF 01, BCF 02, BCF 03, BCF06, BCF 07, BCF 08, BCF09, BCF11, BCF12, BCF13 and BCF14 as well as a series of peptides of the corresponding gp41 dominant region which are called ESS/BCF02, FAN/BCF01, LOB/BCF06, MAN/BCF07, NKO/BCF08, POC/BCF03, NAN/BCF11, BCF09, BCF12, BCF13 and BCF14. A number of these peptides are difficult to handle in diagnosis because of their low solubility, especially the peptide BCF13.

Unexpectedly, it has now been found that certain synthetic peptides are diagnostic reagents of superior quality and they make it possible to satisfactorily screen patients infected with group O HIV-1 retroviruses. These peptides are composed of variable sequences articulated around highly conserved short sequences, which are present in isolates of the group O HIV-1 retroviruses. The peptides of the invention make it possible to obtain results which are quite superior to those obtained with synthetic peptides carrying immunodominant epitopes of the gp41 (env) of certain group O HIV-1 isolates.

Subsequently, to name the amino acids, the three-letter nomenclature will be used.

The synthetic peptides of the invention correspond to the general formula (I): (various regions of SEQ ID NOS 1–16, respectively)

$$\Delta\text{-Z-TrpGlyCys-}\Theta\text{-CysTyrThrSer-}\Omega \qquad \text{(I)}$$

in which:

- Δ represents a biotinyl radical, a biocytinyl radical, a hydrogen atom, an acetyl ($CH_3CO$—) radical, an aliphatic chain which may contain one or two thiol, aldehyde or amine functional groups, the aliphatic chain preferably being an alkyl chain of 1 to 6 carbon atoms or an alkenyl chain of 2 to 6 carbon atoms, or an aminoalkylcarbonyl chain of 2 to 6 carbon atoms,
- Z represents a peptide sequence of one of the formulae (II) to (X):

$$\text{-}\Xi_1\text{Ser-}\Xi_2\text{-} \qquad \text{(II)}$$

$$\text{-Ser-}\Xi_2\text{-} \qquad \text{(III)}$$

$$\text{-}\Xi_1\text{-Ser-} \qquad \text{(IV)}$$

$$\text{-}\Xi_1\text{-Gln-}\Xi_2\text{-} \qquad \text{(V)}$$

$$\text{-Gln-}\Xi_2\text{-} \qquad \text{(VI)}$$

$$\text{-}\Xi_1\text{-Gln-} \qquad \text{(VII)}$$

$$\text{-}\Xi_1\text{-Asn-}\Xi_2\text{-} \qquad \text{(VIII)}$$

$$\text{-Asn-}\Xi_2\text{-} \qquad \text{(IX)}$$

$$\text{-}\Xi_1\text{-Asn-} \qquad \text{(X)}$$

in which:

$\Xi_1$ represents a peptide sequence of 0 to 9 amino acids and $\Xi_2$ represents a peptide sequence of 0 to 5 amino acids, $\Theta$ represents a peptide sequence of formula (XI):

-$(AA_1)$-$(AA_2)$-$(AA_3)$-$(AA_4)$-$(AA_5)$- (XI)

in which:

$(AA_1)$ represents either a lysine residue, or an arginine residue, or an ornithine residue, $(AA_2)$ represents either a glycine residue, or an asparagine residue, $(AA_3)$ represents either a lysine residue, or an arginine residue, or an ornithine residue, $(AA_4)$ represents either a leucine residue, or an alanine residue, or an isoleucine residue, or a glutamine residue, $(AA_5)$ represents either an isoleucine residue, or a valine residue, or a leucine residue, or a threonine residue, or a norleucine residue, or a norvaline residue, provided, however, that $(AA_1)$, $(AA_2)$, $(AA_3)$, $(AA_4)$ and $(AA_5)$ never form together the peptide sequences -Lys Gly Lys Leu Ile-(SEQ ID NO: 17) and -Lys Gly Lys Leu Val-(SEQ ID NO: 18), $\Omega$, attached to the —CO— group of serine, represents:

a hydroxyl (—OH) radical or an amino (—$NH_2$) radical, an alkoxy radical comprising from 1 to 6 carbon atoms, a peptide sequence of formula (XII):

-Val-$\Sigma$-$\Psi$ (XII)

in which $\Sigma$ represents a sequence of formula (XIII) or of formula (XIV):

-$(AA_6)$-Trp Asn-$(AA_7)$-$(AA_8)$ (XIII)

-$(AA_6)$-Trp His-$(AA_7)$-$(AA_8)$ (XIV)

in which:

$(AA_6)$ represents an amino acid different from lysine, $(AA_7)$ represents an amino acid, $(AA_8)$ represents a serine or threonine residue, and $\Psi$, attached to the —CO— residue of the free $AA_8$ amino acid, represents an OH or $NH_2$ group or an alkoxy radical comprising from 1 to 6 carbon atoms, a peptide sequence of formula (XV):

-Val-$\Psi$ (XV)

in which $\Psi$, attached to the —CO— residue of valine, has the same meaning as for the formula (XII), or a peptide sequence of one of the formulae (XVI) to (XVIII): (Varous regions of SEQ ID NOS 1–16, respectively)

-Z-TrpGlyCys-$\Theta$-CysTyrThrSer-$\Psi$ (XVI)

Val-$\Sigma$-Z-TrpGlyCys-$\Theta$-CysTyrThrSerVal-$\Sigma$-$\Psi$ (XVII)

Val-Z-TrpGlyCys-$\Theta$-CysTyrThrSerVal-$\Psi$ (XVIII)

in which Z and $\Theta$ have the definition given for the formula (I) and $\Sigma$ has the definition given for the formula (XII) and $\Psi$, attached to the —CO— residue of serine, on the —CO— residue of the $AA_8$ amino acid or on the —CO— residue of valine, has the same meaning as for the formula (XII).

When $\Omega$ represents a peptide sequence of one of the formulae (XVI) to (XVIII), the peptide of formula (I) becomes a dimer whose size may vary from 26 to 66 amino acids. When $\Omega$ does not represent a peptide sequence of one of the formulae (XVI) to (XVIII), the peptides of formula (I) are of the monomeric type and their size may vary from 13 to 33 amino acids.

The peptides according to the invention may be either in a linear form, or in a form cyclized by means of intercysteine disulphide bridges.

The compounds of formula (I) in which $(AA_5)$ represents either a valine residue, or a leucine residue, or a threonine residue are preferred, and when $\Omega$ corresponds to a peptide sequence of formula (XII), $(AA_6)$ represents either a glutamine residue or an arginine residue.

The peptides of formula (I) are preferred in which:

$\Delta$ represents a biotinyl radical, a hydrogen atom or an aliphatic chain which may contain one or two thiol, aldehyde or amine functional groups, the aliphatic chain preferably being an alkyl chain of 1 to 6 carbon atoms, or an aminoalkylcarbonyl chain of 2 to 6 carbon atoms, Z represents a peptide sequence of formula (II) or (V), in which $\Xi_1$ represents a peptide sequence of two amino acids and $\Xi_2$ represents an amino acid, or a sequence of formula (IV), in which $\Xi_1$ represents three amino acids, or a peptide sequence of formula (VIII), in which $\Xi_1$ represents a peptide sequence of nine, eight or three amino acids and $\Xi_2$ a peptide sequence of five amino acids, $\Theta$ represents a peptide sequence of formula:

-Lys Gly Arg Leu Val-(various regions of SEQ ID NOS, 3, 4, 5, 9, 10, 15 & 16, respectively), -Arg Gly Lys Ala Val-(various regions of SEQ ID NOS 1 & 6, respectively), -Arg Gly Arg Leu Val-(various regions of SEQ ID NOS, 2, 8, 11, 12, & 13, respectively), or -Arg Gly Arg Ala Val-(a region of SEQ ID NO: 14), and $\Omega$ represents a hydroxyl group, the peptide sequence (XV) or one of the following sequences which correspond to the peptide sequence of formula (XII):

-Val Arg Trp Asn Glu Thr-$\Psi$(various regions of SEQ ID NOS 11, 12, & 13, respectively)

-Val Gln Trp Asn Glu Thr-$\Psi$(various regions of SEQ ID NOS, 1, 2, 3, 6, 9, & 8, respectively)

or

-Val Gln Trp Asn Ser Thr-$\Psi$(various regions of SEQ ID NOS 4, & 5, respectively).

Preferably, Z represents a peptide sequence of formula:

-Leu Leu Ser Ser-(various regions of SEQ ID NOS 3, 4, 8 & 9, respectively)

-Leu Leu Asn Ser-(various regions of SEQ ID NOS 6, 10, 11, 14, 15, & 20, respectively)

-Leu Leu Gln Ser-(a region of SEQ ID NO: 5)

-Arg Leu Asn Ser-(a region of SEQ ID NO:16)

-Ala Leu Glu Thr Leu Leu Gln Asn Gln Gln Leu Leu Asn Ser-(a region of SEQ ID:11)

-Ala Leu Glu Thr Leu Leu Gln Asn Gln Gln Leu Leu Asp Leu-(a region of SEQ ID NO: 13)

-Ala Leu Glu Thr Leu Leu Gln Asn Gln Gln Leu Leu Asn Ile-(a region of SEQ ID NOS 14, 15 & 20, respectively)

-Leu Asn Gln Gln Arg Leu Leu Asn Ser-(a region of SEQ ID NOS 14, 15% 20, respectively) or -Arg Ala Leu Glu Thr Leu Leu Asn Gln Gln Arg Leu Leu Asn Ser-(a region of SEQ ID: 15)

Also forming part of the invention are the synthetic peptides comprising from 20 to 50 amino acids and corresponding to the formula (Ia): (various regions of SEQ ID NOS 1–16, respectively)

$$\Delta\text{-}Z_a\text{-TrpGlyCys-}\Theta\text{-CysTyrThrSer-}\Omega_a \quad \text{(Ia)}$$

in which $Z_a$ represents a radical of formulae IIa to Xa:

$$\Xi_{1a}\text{-Ser-}\Xi_{2a} \quad \text{(IIa)}$$

$$\text{-Ser-}\Xi_{2a} \quad \text{(IIIa)}$$

$$\text{-}\Xi_{1a}\text{-Ser} \quad \text{(IVa)}$$

$$\Xi_{1a}\text{-Gln-}\Xi_{2a} \quad \text{(Va)}$$

$$\text{-Gln-}\Xi_{2a} \quad \text{(VIa)}$$

$$\Xi_{1a}\text{-Gln-} \quad \text{(VIIa)}$$

$$\Xi_{1a}\text{-Asn-}\Xi_{2a} \quad \text{(VIIIa)}$$

$$\text{-Asn-}\Xi_{2a} \quad \text{(IXa)}$$

$$\text{-}\Xi_{1a}\text{-Asn} \quad \text{(Xa)}$$

in which:

-$\Xi_{1a}$ represents a peptide sequence of 1 to 5 amino acids and

-$\Xi_{2a}$ an amino acid,

-$\Omega_a$ represents a peptide sequence of formula (XII), as defined for the formula (I), or a peptide sequence of formula (XVIIa): (various regions of SEQ ID NOS 1–16, respectively)

$$\text{Val-}\Sigma\text{-}Z_a\text{-TrpGlyCys-}\Theta\text{-CysTyrThrSerVal-}\Sigma\text{-}\Psi \quad \text{(XVIIa)}$$

in which $Z_a$ has the meaning given for the formula (Ia) and

Δ, Θ, Σ and Ψ have the same meaning as for the formula (I):

The peptides of formula (I) or (Ia) including one of the following sequences (these peptides may be of the dimer type or of the monomer type as defined above) are preferred. The sequences are given according to the one- and three-letter nomenclatures:

```
(SEQ ID NO: 1)

-LLSLWGCRGKAVCYTSVQWNET- or

-Leu Leu Ser Leu Trp Gly Cys Arg Gly Lys Ala Val Cys Tyr Thr Ser Val Gln Trp Asn
  1             5                   10                  15                  20

Glu Thr-
    22

(SEQ ID NO: 2)
-LLSLWGCRGRLVCYTSVQWNET- or

-Leu Leu Ser Leu Trp Gly Cys Arg Gly Arg Leu Val Cys Tyr Thr Ser Val Gln Trp Asn
  1             5                   10                  15                  20

Glu Thr-
    22

(SEQ ID NO: 3)
-LLSSWGCKGRLVCYTSVQWNET- or

-Leu Leu Ser Ser Trp Gly Cys Lys Gly Arg Leu Val Cys Tyr Thr Ser Val Gln Trp Asn
  1               5                 10                  15                  20

Glu Thr-
    22

(SEQ ID NO: 4)
-LLSSWGCKGRLVCYTSVQWNST- or

-Leu Leu Ser Ser Trp Gly Cys Lys Gly Arg Leu Val Cys Tyr Thr Ser Val Gln Trp Asn
  1               5                 10                  15                  20

Ser Thr-
    22

(SEQ ID NO: 5)

-LLQSWGCKGRLVCYTSVQWNST- or

-Leu Leu Gln Ser Trp Gly Cys Lys Gly Arg Leu Val Cys Tyr Thr Ser Val GIn Trp Asn
  1             5                   10                  15                  20
```

-continued

Ser Thr-
22

(SEQ ID NO: 6)

-LLNSWGCRGKAVCYTSVQWNET- or

-Leu Leu Asn Ser Trp Gly Cys Arg Gly Lys Ala Val Cys Tyr Thr Ser Val Gln Trp Asn
1 5 10 15 20

Glu Thr-
22

(SEQ ID NO: 7)
-LLSLWGCRGRAVCYTSVQWNET- or

-Leu Leu Ser Leu Trp Gly Cys Arg Gly Arg Ala Val Cys Tyr Thr Ser Val Gln Trp Asn
1 5 10 15 20

Glu Thr-
22

(SEQ ID NO: 8)

-LLSSWGCRGRLVCYTSVQWNET- or

-Leu Leu Ser Ser Trp Gly Cys Arg Gly Arg Leu Val Cys Tyr Thr Ser Val Gln Trp Asn
1 5 10 15 20

Glu Thr-
22

(SEQ ID NO: 9)

-LLSSWGCKGRLVCYTS- or

-Leu Leu Ser Ser Trp Gly Cys Lys Gly Arg Leu Val Cys Tyr Thr Ser-
1 5 10 15

(SEQ ID NO: 10)

-LLNSWGCKGRLVCYTS- or

-Leu Leu Asn Ser Trp Gly Cys Lys Gly Arg Leu Val Cys Tyr Thr Ser-
1 5 10 15

(SEQ ID NO: 11)

-ALETLLQNQQLLNSWGCRGRLVCYTSVRWNET- or

-Ala Leu Glu Thr Leu Leu Gln Asn Gln Gln Leu Leu Asn Ser Trp Gly Cys Arg Gly
1 5 10 15

Arg Leu Val Cys Tyr Thr Ser Val Arg Trp Asn Glu Thr-
20 25 30

(SEQ ID NO: 12)

-ALETLLQNQQLLNIWGCRGRLVCYTSVRWNET- or

-Ala Leu Glu Thr Leu Leu Gln Asn Gln Gln Leu Leu Asn Ile Trp Gly Cys Arg Gly
1 5 10 15

Arg Leu Val Cys Tyr Thr Ser Val Arg Trp Asn Glu Thr-
20 25 30

(SEQ ID NO: 13)

-ALETLLQNQQLLDLWGCRGRLVCYTSVRWNET- or

-Ala Leu Glu Thr Leu Leu Gln Asn Gln Gln Leu Leu Asp Leu Trp Gly Cys Arg Gly
1 5 10 15

Arg Leu Val Cys Tyr Thr Ser Val Arg Trp Asn Glu Thr-
20 25 30

(SEQ ID NO: 14)

-LNQQRLLNSWGCKGRLVCYTSV- or

-continued

```
-Leu Asn Gln Gln Arg Leu Leu Asn Ser Trp Gly Cys Lys Gly Arg Leu Val Cys Tyr
  1             5                   10                  15

Thr Ser Val-
20
```

(SEQ ID NO: 15)

-RALETLLNQQRLLNSWGCKGRLVCYTSV- or

```
-Arg Ala Leu Glu Thr Leu Leu Asn Gln Gln Arg Leu Leu Asn Ser Trp Gly Cys Lys
  1             5               10                      15

Gly Arg Leu Val Cys Tyr Thr Ser Val-
20                  25
```

(SEQ ID NO: 16)

-RLNSWGCKGRLVCYTSV- or

```
-Arg Leu Asn Ser Trp Gly Cys Lys Gly Arg Leu Val Cys Tyr Thr Ser Val-
  1              5                  10                  15
```

PEPTIDE No. 1 (2B): SEQ ID NO: 1

LLSLWGCRGKAVCYTSVQWNET or

```
Leu Leu Ser Leu Trp Gly Cys Arg Gly Lys Ala Val Cys Tyr Thr Ser Val Gln Trp Asn
 1              5                  10                  15                  20

Glu Thr
    22
```

PEPTIDE No. 2 (3B): SEQ ID NO: 2

LLSLWGCRGRLVCYTSVQWNET or

```
Leu Leu Ser Leu Trp Gly Cys Arg Gly Arg Leu Val Cys Tyr Thr Ser Val Gln Trp Asn
 1              5                  10                  15                  20

Glu Thr
    22
```

PEPTIDE No. 3 (4B): SEQ ID NO: 3

LLSSWGCKGRLVCYTSVQWNET or

```
Leu Leu Ser Ser Trp Gly Cys Lys Gly Arg Leu Val Cys Tyr Thr Ser Val Gln Trp Asn
 1              5                  10                  15                  20

Glu Thr
    22
```

PEPTIDE No. 4 (5B): SEQ ID NO: 4

LLSSWGCKGRLVCYTSVQWNST or

```
Leu Leu Ser Ser Trp Gly Cys Lys Gly Arg Leu Val Cys Tyr Thr Ser Val Gln Trp Asn
 1              5                  10                  15                  20

Ser Thr
    22
```

PEPTIDE No. 5 (6B): SEQ ID NO: 5

LLQSWGCKGRLVCYTSVQWNST or

```
Leu Leu Gln Ser Trp Gly Cys Lys Gly Arg Leu Val Cys Tyr Thr Ser Val Gln Trp Asn
 1              5                  10                  15                  20

Ser Thr
    22
```

PEPTIDE No. 6: SEQ ID NO: 6

LLNSWGCRGKAVCYTSVQWNET or

```
Leu Leu Asn Ser Trp Gly Cys Arg Gly Lys Ala Val Cys Tyr Thr Ser Val Gln Trp Asn
 1              5                  10                  15                  20
```

-continued

```
Glu Thr
    22

PEPTIDE No. 7: SEQ ID NO: 7

LLSLWGCRGRAVCYTSVQWNET or

Leu Leu Ser Leu Trp Gly Cys Arg Gly Arg Ala Val Cys Tyr Thr Ser Val Gln Trp Asn
 1              5                   10                  15                  20

Glu Thr
    22

PEPTIDE No. 8 (7B): SEQ ID NO: 8

LLSSWGCRGRLVCYTSVQWNET or

Leu Leu Ser Ser Trp Gly Cys Arg Gly Arg Leu Val Cys Tyr Thr Ser Val Gln Trp Asn
 1              5                   10                  15                  20

Glu Thr
    22

PEPTIDE No. 9 (12B): SEQ ID NO: 9

LLSSWGCKGRLVCYTS or

Leu Leu Ser Ser Trp Gly Cys Lys Gly Arg Leu Val Cys Tyr Thr Ser
 1              5                   10                  15

PEPTIDE No. 10 (14B): SEQ ID NO: 10

LLNSWGCKGRLVCYTS or

Leu Leu Asn Ser Trp Gly Cys Lys Gly Arg Leu Val Cys Tyr Thr Ser
 1              5                   10                  15

PEPTIDE No. 11 (18B): SEQ ID NO: 11

ALETLLQNQQLLNSWGCRGRLVCYTSVRWNET or

Ala Leu Glu Thr Leu Leu Gln Asn Gln Gln Leu Leu Asn Ser Trp Gly Cys Arg Gly
 1              5                   10                  15

Arg Leu Val Cys Tyr Thr Ser Val Arg Trp Asn Glu Thr
20                  25                  30

PEPTIDE No. 12 (19B): SEQ ID NO: 12

ALETLLQNQQLLNIWGCRGRLVCYTSVRWNET or

Ala Leu Glu Thr Leu Leu Gln Asn Gln Gln Leu Leu Asn Ile Trp Gly Cys Arg Gly
 1              5                   10                  15

Arg Leu Val Cys Tyr Thr Ser Val Arg Trp Asn Glu Thr
20                  25                  30

PEPTIDE No. 13 (20B): SEQ ID NO: 13

ALETLLQNQQLLDLWGCRGRLVCYTSVRWNET or

Ala Leu Glu Thr Leu Leu Gln Asn Gln Gln Leu Leu Asp Leu Trp Gly Cys Arg Gly
 1              5                   10                  15

Arg Leu Val Cys Tyr Thr Ser Val Arg Trp Asn Glu Thr
20                  25                  30

PEPTIDE No. 14 (21B): SEQ ID NO: 14

LNQQRLLNSWGCKGRLVCYTSV or

Leu Asn Gln Gln Arg Leu Leu Asn Ser Trp Gly Cys Lys Gly Arg Leu Val Cys Tyr
 1             5                    10                  15

Thr Ser Val
20

PEPTIDE No. 15 (22B): SEQ ID NO: 15

RALETLLNQQRLLNSWGCKGRLVCYTSV or
```

-continued

```
Arg Ala Leu Glu Thr Leu Leu Asn Gln Gln Arg Leu Leu Asn Ser Trp Gly Cys Lys
 1               5                   10                  15

Gly Arg Leu Val Cys Tyr Thr Ser Val
20                  25
```

PEPTIDE No. 16 (23B): SEQ ID NO: 16

RLNSWGCKGRLVCYTSV or

```
Arg Leu Asn Ser Trp Gly Cys Lys Gly Arg Leu Val Cys Tyr Thr Ser Val
 1               5                   10                  15
```

The synthetic peptides of formula (I), which are the subject of the present invention, can be obtained by solid phase synthesis according to conventional methods: R. B. Merrifield, *J. Amer. Chem. Soc.* (1963), 85, pp. 2149–2154; R. C. Sheppard, in "Peptides 1971", Nesvadba H. (ed.) North Holland, Amsterdam, pp. 111; E. Atherton and R. L. Sheppard, in "*Solid phase peptide synthesis, a practical approach*", IRL PRESS, (1989), Oxford University Press, pp. 25–34. As automatic synthesizer, it is possible to use the synthesizer "9050 Plus Pep Synthesizer" from Millipore or an equivalent synthesizer.

The solid support used for the syntheses should be compatible with the technique and the chemistry used. For example, for a synthesis on the synthesizer "9050 Plus pep. Synthesizer", it is recommended to use a resin suitable for the so-called "continuous flow" technique; the PEG PS resins meet these criteria. These supports consist of an arm ("spacer") based on polyethylene glycol (PEG) situated between the functional group of the polystyrene beads and the point of attachment of the first amino acid. The nature of this point of anchorage may vary according to the C-terminal functional group chosen. In the present case, various PEG-PS resins were used.

The starting resin and the amino acids used as raw materials are products which are commercially available (PerSeptive-Biosystem, or Neosystem).

For the peptide synthesis, the following side chain protecting groups were used:

| Amino acids | Protecting group |
|---|---|
| Arginine | Pentamethyl-2,2,4,6,7-dihydrobenzofuran-5-sulphonyl (Pbf) |
| Asparagine, Glutamine | Trityl (Trt) |
| Cysteine | Trityl (Trt) or Acetamidomethyl (Acm) |
| Serine, Threonine, Tyrosine | tert-Butyl ether (tBu) |
| Lysine, Tryptophan | tert-Butyloxycarbonyl (Boc) |

The temporary protection of the primary amine functional group at the α position of the amino acids which is used is the 9-fluorenylmethyloxylcarbonyl (Fmoc) group. The deprotection is carried out with a 20% solution of piperidine in dimethylformamide.

For the coupling, an excess of diisopropylcarbodiimide (DIPCDI) and 1-hydroxybenzotriazole (HOBt) is preferably used.

After synthesis, the resin is washed with organic solvents (dimethylformamide, followed by dichloromethane), dried under vacuum and then treated with a trifluoroacetic acid (TFA)-based solution cooled to 0° C. and containing appropriate "scavengers". There may be used, for example, the K reagent containing 82% of trifluoroacetic acid, 5% of phenol, 5% of water, 5% of thioanisole and 3% of ethanedithiol.

After filtration of the resin, the synthetic peptides are precipitated and rinsed with ether.

The synthetic peptides are then purified by reversed phase liquid chromatography and their purity is determined by mass spectrometry. As solid phase, it is possible to use, for example, the Bondapak C-18 phase. The peptides are eluted by forming a linear gradient between two buffer solutions, the first which is essentially aqueous (for example water-TFA 0.1%) and the second which is rather organic (for example a mixture containing 60% acetonitrile, 39.92% water and 0.08% TFA). The pure fractions collected are combined, concentrated under vacuum and freeze-dried.

For the cyclization, the purified synthetic peptides are dissolved in an ammonium acetate solution (10 mM). The pH is adjusted to 8.5 by addition of 1 M ammonium hydroxide. The solution is vigorously stirred. The cyclization is complete after 18 hours. The pH is then reduced to 6 by addition of acetic acid. The cyclized peptides are freeze-dried and then purified by reversed phase liquid chromatography as described above.

The immunoreactivity of the peptides of the invention was evaluated with the aid of sera from patients predominantly of Cameroonian origin infected with group O HIV-1 retroviruses. The various tests carried out demonstrated that the peptides of the invention, alone or in combination (compositions of peptides), make it possible to detect 100% of the sera infected with group O HIV-1 retroviruses.

The synthetic peptides of the invention therefore find application in immunological tests for the screening of infections due to group O HIV-1 retroviruses. It is also possible to use combinations of several synthetic peptides of formula I. These combinations, which may contain two or more peptides of formula I, also form part of the invention. Combinations containing peptides No. 1 (2B) and No.3 (4B) are preferred.

It is also possible to use synthetic peptides of formula (I) of the present invention in combination with group O HIV-1 recombinant peptides (recombinant proteins) as can be obtained by conventional methods and having the sequences described, for example in application EP 0,591,914. Such compositions are also within the scope of the present invention.

The synthetic peptides of the invention can also be used in combination with other HIV-2 and/or HIV-1 recombinant (recombinant proteins) or synthetic peptides, such as the peptides described in patent applications or patents EP 0,387,914, EP 0,239,425, EP 0,220,273 or EP 0,267,802. This list of patent applications or patents is not exhaustive and is given by way of example.

The compositions containing one or more synthetic peptides of formula (I) and one or more HIV-1 or HIV-2 recombinant or synthetic peptides find application in diagnosis for the screening of patients infected with various HIV retroviruses. These compositions also form part of the present invention.

Immunoassay methods using one or more synthetic peptides of formula (I), alone or in combination with group O HIV-1 recombinant peptides or HIV-1 and/or HIV-2 recombinant or synthetic peptides, also form part of the invention.

The invention also relates to kits, for carrying out immunoassays, which include a peptide of formula (I) or a composition which contains at least one peptide of formula (I).

The following examples illustrate the invention and are given with no limitation being implied.

EXAMPLE 1

Preperation of a Compound According to the Invention; PEPTIDE No. 2 (3B) (SEQ ID NO: 2)

```
Preparation of a compound according to the invention:
PEPTIDE No. 2 (3B) (SEQ ID NO: 2)

LLSLWGCRGRLVCYTSVQWNET or

Leu Leu Ser Leu Trp Gly Cys Arg Gly Arg Leu Val Cys Tyr Thr Ser Val Gln Trp Asn
 1              5                   10                  15                  20

Glu Thr
    22
```

This peptide was synthesized on a solid phase. The technique developed in 1963 by Merrifield (*J. Am. Chem. Soc.* (1963) 85, pp. 2149–2154) consists in attaching the first amino acid onto a polymeric solid support (resin) by its acid functional group and in extending the peptide sequence from this first amino acid, the peptide being synthesized remaining anchored on the resin.

For the synthesis of peptide No. 2, there were used, as synthesizer, the synthesizer “9050 Plus Pep Synthesizer” and as resin, the resin Fmoc Thr (OtBu) PEG PS.

The various steps of the synthesis are summarized in Table I below:

TABLE I

| AMINO ACID RESIDUE | $NH_2$ PROTECTION | SIDE PROTECTION | COUPLING METHOD | EQ NUMBER - DURATION OF COUPLING |
|---|---|---|---|---|
| Glu | Fmoc | OtBu | DIPCDI/HOBt | 5 eq - 30 min |
| Asn | Fmoc | Trt | DIPCDI/HOBt | 5 eq - 30 min |
| Trp | Fmoc | Boc | DIPCDI/HOBt | 5 eq - 30 min |
| Gln | Fmoc | Trt | DIPCDI/HOBt | 5 eq - 30 min |
| Val | Fmoc | | DIPCDI/HOBt | 5 eq - 30 min |
| Ser | Fmoc | tBu | DIPCDI/HOBt | 5 eq - 30 min |
| Thr | Fmoc | tBu | DIPCDI/HOBt | 5 eq - 30 min |
| Tyr | Fmoc | tBu | DIPCDI/HOBt | 5 eq - 30 min |
| Cys | Fmoc | Trt | DIPCDI/HOBt | 5 eq - 30 min |
| Val | Fmoc | | DIPCDI/HOBt | 5 eq - 30 min |
| Leu | Fmoc | | DIPCDI/HOBt | 5 eq - 30 min |
| Arg | Fmoc | Pbf | DIPCDI/HOBt | 5 eq - 30 min |
| Gly | Fmoc | | DIPCDI/HOBt | 5 eq - 30 min |
| Arg | Fmoc | Pbf | DIPCDI/HOBt | 5 eq - 30 min |
| Cys | Fmoc | Trt | DIPCDI/HOBt | 5 eq - 30 min |
| Gly | Fmoc | | DIPCDI/HOBt | 5 eq - 30 min |
| Trp | Fmoc | Boc | DIPCDI/HOBt | 5 eq - 30 min |
| Leu | Fmoc | | DIPCDI/HOBt | 5 eq - 30 min |
| Ser | Fmoc | tBu | DIPCDI/HOBt | 5 eq - 30 min |
| Leu | Fmoc | | DIPCDI/HOBt | 5 eq - 30 min |
| Leu | Fmoc | | DIPCDI/HOBt | 5 eq - 30 min |

At the end of the synthesis, the resin was washed with dimethylformamide and then dichloromethane and dried under vacuum.

Next, the resin was treated with the K reagent (82% trifluoroacetic acid; 5% phenol; 5% water; 5% thioanisole; 3% ethanedithiol). Peptide No. 2 (3B), isolated by precipitation with the aid of diethyl ether, was then rinsed with the same solvent. 140 mg of peptide No. 2 (3B) were thus obtained.

Peptide No. 2 (3B) was then purified by reversed phase liquid chromatography. The Bondapak C-18 phase was used as solid phase. The peptide was eluted by forming a linear gradient between two buffer solutions, the first which is essentially aqueous (for example water-TFA 0.1%) and the second which is rather organic (for example a mixture containing: 60% acetonitrile, 39.92% water and 0.08% TFA). The pure fractions collected were combined, concentrated under vacuum and freeze-dried.

For the cyclization, the purified synthetic peptide thus obtained was dissolved in an ammonium acetate solution (10 mM). The pH was adjusted to 8.5 by addition of 1 M ammonium hydroxide. The solution was vigorously stirred. The cyclization was complete after 18 hours. The pH was then reduced to 6 by addition of acetic acid. The cyclized peptide was freeze-dried and then purified by reversed phase liquid chromatography as described above.

Preparation of a Compound According to the Invention: PEPTIDE No. 15 (22B)

This peptide was synthesized as peptide No. 2 (3B), but using as resin the resin FmocPAL PEG-PS.

The various steps of the synthesis are summarized in Table II below:

TABLE II

| AMINO ACID RESIDUE | $NH_2$ PROTECTION | SIDE PROTECTION | COUPLING METHOD | EQ NUMBER - DURATION OF COUPLING |
|---|---|---|---|---|
| Val | Fmoc | | DIPCDI/HOBt | 5 eq - 45 mn |
| Ser | Fmoc | tBu | DIPCDI/HOBt | 5 eq - 45 mn |
| Thr | Fmoc | tBu | DIPCDI/HOBt | 5 eq - 45 mn |
| Tyr | Fmoc | tBu | DIPCDI/HOBt | 5 eq - 45 mn |
| Cys | Fmoc | Trt | DIPCDI/HOBt | 5 eq - 45 mn |
| Val | Fmoc | | DIPCDI/HOBt | 5 eq - 45 mn |
| Leu | Fmoc | | DIPCDI/HOBt | 5 eq - 45 mn |
| Arg | Fmoc | Pbf | DIPCDI/HOBt | 5 eq - 45 mn |
| Gly | Fmoc | | DIPCDI/HOBt | 5 eq - 45 mn |
| Lys | Fmoc | Boc | DIPCDI/HOBt | 5 eq - 45 mn |
| Cys | Fmoc | Trt | DIPCDI/HOBt | 5 eq - 45 mn |
| Gly | Fmoc | | DIPCDI/HOBt | 5 eq - 45 mn |
| Trp | Fmoc | Boc | DIPCDI/HOBt | 5 eq - 45 mn |
| Ser | Fmoc | tBu | DIPCDI/HOBt | 5 eq - 45 mn |
| Asn | Fmoc | Trt | DIPCDI/HOBt | 5 eq - 45 mn |
| Leu | Fmoc | | DIPCDI/HOBt | 5 eq - 45 mn |
| Leu | Fmoc | | DIPCDI/HOBt | 5 eq - 45 mn |
| Arg | Fmoc | Pbf | DIPCDI/HOBt | 5 eq - 45 mn |
| Gln | Fmoc | Trt | DIPCDI/HOBt | 5 eq - 45 mn |
| Gln | Fmoc | Trt | DIPCDI/HOBt | 5 eq - 45 mn |
| Asn | Fmoc | Trt | DIPCDI/HOBt | 5 eq - 45 mn |
| Leu | Fmoc | | DIPCDI/HOBt | 5 eq - 45 mn |
| Leu | Fmoc | | DIPCDI/HOBt | 5 eq - 45 mn |
| Thr | Fmoc | tBu | DIPCDI/HOBt | 5 eq - 45 mn |
| Glu | Fmoc | OtBu | DIPCDI/HOBt | 5 eq - 45 mn |
| Leu | Fmoc | | DIPCDI/HOBt | 5 eq - 45 mn |

TABLE II-continued

| AMINO ACID RESIDUE | $NH_2$ PRO-TECTION | SIDE PRO-TECTION | COUPLING METHOD | EQ NUMBER - DURATION OF COUPLING |
|---|---|---|---|---|
| Ala | Fmoc | | DIPCDI/HOBt | 5 eq - 45 mn |
| Arg | Fmoc | Pbf | DIPCDI/HOBt | 5 eq - 45 mn |

At the end of the synthesis, the resin was washed with dimethylformamide, followed by dichloromethane and dried under vacuum.

Next, the resin was treated with the K reagent (82% trifluoroacetic acid; 5% phenol; 5% water; 5% thioanisole; 3% ethanedithiol). The peptide No.7 (22B) isolated by precipitation with the aid of diethyl ether was then rinsed with the same solvent. 140 mg of peptide No. 15 (22B) were thus obtained.

Peptide No. 15 (22B) was then purified by reversed phase liquid chromatography and then cyclized, freeze-dried and purified as described above for peptide No. 2 (3B).

In the same manner, and using the appropriate resins and amino acids, the other compounds of the invention were synthesized.

Table III indicates the molecular weight of some peptides of formula (I), in non-cyclized form, evaluated by mass spectrometry.

TABLE III

| Peptide No. | Molecular weight (Daltons) |
|---|---|
| 1 (2B) | 2512 |
| 2 (3B) | 2583 |
| 3 (4B) | 2528 |
| 4 (5B) | 2586 |
| 5 (6B) | 2527 |
| 9 (12B) | 1772 |
| 10 (14B) | 1799 |
| 11 (18B) | 3752 |
| 12 (19B) | 3778 |
| 13 (20B) | 3780 |
| 14 (21B) | 2538 |
| 15 (22B) | 3222 |
| 16 (23B) | 1941 |

EXAMPLE 2

Evaluation of the Immunoreactivity of the Peptides According to the Invention by the Immunoenzymatic Test: Test No. 1

The sera used ESS, DUR, VAU and HAD are sera from French patients infected with group O HIV-1 retroviruses. The other serum samples from patients infected with group O HIV-1 retroviruses were obtained by the Yaoundé Pasteur Centre in Cameroon and were serotyped group O according to the serological algorithm described in *AIDS* (1977), 11, pp 445–453.

The HIV-negative sera (n=48) were obtained from healthy volunteers.

The synthetic peptides used were dissolved in water at a concentration of 1 mg/ml (stock solution). For the solid phase sensitization step (coating), 110 µl of a solution at 2 µg/ml of each peptide (obtained by diluting the stock solution with 0.1 M carbonate buffer solution) were added to each well of the microtitre plates Microtiter™ (NUNC). After incubating overnight at room temperature, the microplates were first washed with a Tris-NaCl buffer solution pH 7.4 containing 0.1% of Tween® 20 and 0.001% sodium merthiolate, and then saturated with a PBS solution containing 0.5% of Régilait™ (dried skimmed milk). After aspirating the saturating solution, the plates were heated for 10 min at 50° C.

The serum samples were diluted 1/5 with a skimmed milk solution (citrate buffer supplemented with 0.01% of phenol red, 0.25% of chloroform and 0.25% of Kathon®), deposited in the wells of the plates and incubated for 30 min at 40° C.

After washing with a Tris-NaCl buffer solution pH 7.4 containing 0.1% of Tween® 20 and 0.001% of sodium merthiolate, 100 µl of a solution of conjugate consisting of horseradish peroxidase-labelled anti-human IgG and IgM goat antibodies, containing as preservative 0.01% of sodium merthiolate, in solution in a citrate buffer solution supplemented with 30% glycerol and 25% normal foetal calf serum, were added to each plate well and then the plates were incubated for 30 min at 40° C.

After washing with a Tris-NaCl buffer solution pH 7.4 containing 0.1% of Tween® 20 and 0.001% of sodium merthiolate, the colour was developed by adding, to each well, 100 µl of O-phenylenediamine in solution in hydrogen peroxide. The microplates were then incubated for 30 min at room temperature and in the dark. The coloured reaction was then stopped by addition of 100 µl of 4N sulphuric acid. The absorbance (A) was determined at 490 and 620 nm.

The relative absorbance (A490–A620) read in each well is proportional to the immunoreactivity of each peptide. It indicates the ability of each peptide to react with the biological sample with which the test is carried out. The cut-off value was determined as being an absorbance equal to 0.15. It corresponds to the mean of the negative values (n=48) plus 12 standard deviations.

The reactivity of the peptides of the invention (peptide No. 3 (4B), peptide No. 2 (3B) and peptide No. 1 (2B), all in cyclized form), was compared with that of two synthetic peptides having, as sequence, a portion of the natural sequence of the envelope (env) of the VAU isolate (group O HIV-1 retrovirus) and comprising an immunodominant epitope of gp41.

These two peptides have the following sequence:

```
VAU 22 AA (SEQ ID NO: 19)

Leu Leu Asn Leu Trp Gly Cys Lys Asn Arg Ala Ile Cys Tyr Thr Ser Val Lys Trp Asn
 1              5                   10                  15                  20

Lys Thr
    22

VAU 35 AA (SEQ ID NO: 20)
```

-continued

```
Arg Leu Leu Ala Leu Glu Thr Phe Ile Glu Glu Asn Glu Leu Leu Asn Leu Trp Gly Cys
 1               5                  10                  15                  20

Lys Asn Arg Ala Ile Cys Tyr Thr Ser Val Lys Trp Asn Lys Thr
                25                  30                  35
```

For the study, these peptides were used in cyclized form. The results of this study are indicated in Table IV.

TABLE IV

| | ABSORBANCE | | | | |
|---|---|---|---|---|---|
| SERUM | PEPTIDE No. 3 (4B) | PEPTIDE No. 2 (3B) | PEPTIDE No. 1 (2B) | VAU 22 AA | VAU 35 AA |
| ESS* | >** | > | 2.494 | > | > |
| DUR* | > | > | > | 0.118 | 0.872 |
| HAD | > | 0.518 | 0.041 | 0.789 | 0.871 |
| VAU* | 1.342 | > | > | > | > |
| 3935 | > | 0.893 | 0.307 | 0.138 | 0.227 |
| 6891 | > | 0.614 | 0.062 | 0.359 | 0.496 |
| 6512* | 0.746 | 0.785 | > | 0.120 | 0.174 |
| 1105* | 1.421 | 1.031 | > | 0.099 | 0.129 |
| 4021* | 0.430 | 0.119 | > | 0.050 | 1.957 |
| 5969* | > | 0.282 | > | 2.491 | > |
| 2700 | > | 0.274 | > | > | > |
| 5453 | 0.555 | 0.081 | > | 1.267 | 1.482 |
| 5931 | > | > | > | 0.202 | 2.225 |
| 3136 | > | 0.992 | 0.302 | > | > |
| 3653 | 1.352 | > | 0.044 | 1.441 | 1.322 |
| 2352 | > | > | 0.205 | > | > |
| 3016 | > | > | 0.243 | > | > |
| 3302 | > | > | 0.386 | > | > |
| 2294 | > | > | 0.447 | > | > |
| 3771 | > | > | 0.544 | > | > |
| 1581 | > | > | > | 1.112 | 0.894 |
| 5373 | > | > | > | 1.359 | 0.856 |
| 7443 | > | > | > | 0.920 | 0.574 |
| 3637 | > | > | > | 0.779 | 1.647 |
| 6295* | 1.718 | 1.063 | > | 0.972 | > |
| 6689* | 0.710 | > | > | > | > |
| 1754 | > | > | > | 1.263 | 1.948 |
| 4489* | > | > | > | 1.318 | 1.718 |
| 4364 | > | > | 1.382 | > | > |
| 3884* | > | > | 1.839 | > | > |
| 3529 | > | > | 1.803 | > | > |
| 3482 | 2.402 | > | 1.473 | > | > |
| 1702 | > | > | 1.162 | > | > |
| 6487 | > | 1.017 | 2.687 | 2.889 | 2.891 |
| 5164 | > | > | > | > | > |
| 5766* | > | > | > | > | > |
| 3945 | > | > | > | > | > |
| 4434 | > | > | > | 2.273 | > |
| 4288* | > | > | 2.802 | 2.337 | N.T.*** |
| 6782 | > | 2.091 | 2.462 | 2.190 | 2.214 |
| 2313 | > | > | > | > | > |
| 2312 | > | > | > | > | > |
| 1062 | > | > | > | > | > |
| 402 | > | > | > | > | > |
| 134 | > | > | > | > | > |
| 7120 | > | > | > | > | > |
| 7212 | > | > | > | > | > |
| 6976* | > | > | > | > | > |
| 3600* | > | > | 2.743 | > | > |
| 3236 | > | > | > | > | > |
| 3235 | > | > | > | > | > |
| 2551 | > | > | > | > | > |
| 5270* | > | > | > | > | > |
| 5210 | > | > | > | > | > |
| 5149* | > | > | > | > | > |
| 4477 | > | > | > | 2.511 | > |
| 3891 | > | > | 2.780 | > | > |
| 3627* | > | > | 2.910 | > | > |
| 7258* | > | > | 2.477 | > | > |
| 7007 | 2.136 | 2.334 | > | > | 2.151 |
| 6697 | > | > | > | > | > |

TABLE IV-continued

| | ABSORBANCE | | | | |
|---|---|---|---|---|---|
| SERUM | PEPTIDE No. 3 (4B) | PEPTIDE No. 2 (3B) | PEPTIDE No. 1 (2B) | VAU 22 AA | VAU 35 AA |
| 6998 | > | > | > | > | > |
| 6627 | > | > | > | > | > |
| 6198* | > | > | > | > | > |
| 6165 | > | > | 2.714 | > | > |
| 7439 | > | > | > | > | > |
| 7297* | > | > | > | > | > |
| 6111 | > | > | > | > | > |
| 625 | > | > | > | > | 2.585 |

*serotypes/genotypes
**> = signal greater than the reading capacity of the spectrophotometer.
***Not tested The results of Table IV demonstrate that peptide No. 3 (4B) exhibits the best performance with regard to that noted for the other peptides. This peptide allows the best discrimination between the sera of patients infected with group O HIV-1 retroviruses compared with the two peptides having a portion of the sequence of the VAU isolate corresponding to the immunodominant epitope of gp41. Moreover, peptide No. 2 (3B) and No. 1 (2B) of the invention are more immunoreactive than the VAU 22 AA peptide which comprises the same number of amino acids.

EXAMPLE 3

Evaluation, by an Immunoenzymatic Test, of the Immuno-reactivity of the Peptides According to the Invention: Test No. 2

The serum samples from patients infected with group O HIV-1 retroviruses were obtained by the Yaounde Pasteur Centre in Cameroon and were serotyped group O according to the serological algorithm described in *AIDS* (1977), 11, pp. 445–453. A genotyped sample (Maryland) is obtained from the United States. These samples were previously diluted in negative human serum at the dilutions given in Table V, in order to have a sufficient volume for the different immunoreactivity tests.

The synthetic peptides used were dissolved in water at a concentration of 1 mg/ml (stock solution). For the solid phase sensitization step ("coating"), the procedure was carried out as described for Example 2.

The serum samples were diluted 1/5 with a skimmed milk solution (citrate buffer supplemented with 0.01% of phenol red, 0.25% of chloroform and 0.25% of Kathon®), deposited in the wells of plates and incubated for 30 min at 40° C.

After washing with a Tris-NaCl buffer solution pH 7.4 containing 0.1% of Tween® 20 and 0.001% of sodium merthiolate, 100 μl of a solution of conjugate consisting of horseradish peroxidase-labelled anti-human IgG and IgM goat antibodies, containing as preservative 0.01% of sodium merthiolate, in solution in a citrate buffer solution supplemented with 30% glycerol and 25% normal foetal calf serum, were added to each well of the plates and then they were incubated for 30 min at 40° C.

After washing with a Tris-NaCl buffer solution pH 7.4 containing 0.1% of Tween® 20 and 0.001% of sodium merthiolate, the colour was developed as described in Example 2.

The relative absorbance (OD) (A490–A620) read in each well is proportional to the immunoreactivity of each peptide. It indicates the ability of each peptide to react with the biological sample with which the test is carried out.

The reactivity of the peptides of the invention, peptides No. 10 (14B), No. 11 (18B), No. 12 (19B), No. 14 (21B), No. 15 (22B), No. 16 (23B) all in cyclized form, was compared with that of three homologous synthetic peptides having, as sequence, a portion of the natural sequence of the envelope (env) of a group O HIV-1 retrovirus. These peptides are two peptides derived from the VAU isolate—the peptide VAU 22 AA and the peptide VAU 35 AA—and the peptide MVP 5180 (designated "MVP 5180" in Table V). The peptides VAU 22 AA and VAU 35 AA (whose structure is indicated in Example 2) and the peptide MVP 5180 comprise an immunodominant epitope of gp41.

All these peptides were used in cyclized form. The sequence of the MVP 5180 peptide is the following:

```
MVP 5180 (SEQ ID NO: 21)

Arg Leu Gln Ala Leu Glu Thr Leu Ile Gln Asn Gln Gln Arg Leu Asn Leu Trp Gly Cys
 1               5                  10                  15                  20

Lys Gly Lys Leu Ile Cys Tyr Thr Ser Val Lys Trp Asn Thr Ser
                25                  30                  35
```

The results of this study are indicated in Table V.

TABLE V

| | PEPTIDES* | | | | | | | | |
|---|---|---|---|---|---|---|---|---|---|
| SERUM | No. 10 | No. 11 | No. 12 | No. 14 | No. 15 | No. 16 | MVP 5180 | VAU 35 AA | VAU 22 AA |
| | ABSORBANCE (OD) | | | | | | | | |
| 4280 at 1/50 | 0.022 | 0.686 | 0.201 | 0.286 | 0.689 | 0.033 | 0.382 | 0.013 | 0.021 |
| NGO at 1/50 | 0.067 | 0.335 | 0.193 | 0.157 | 0.315 | 0.110 | 0.184 | 0.055 | 0.040 |
| NJEM at 1/100 | 0.032 | 0.811 | 0.391 | 0.277 | 0.939 | 0.025 | 0.146 | 0.159 | 0.024 |
| MBASSI at 1/100 | 1.217 | 1.150 | 0.747 | 2.134 | 2.010 | 2.683 | 0.248 | 0.120 | 0.257 |
| WANG at 1/50 | 0.698 | 0.234 | 0.124 | 2.397 | 2.680 | 1.290 | 0.075 | 0.025 | 0.041 |
| 258 OUDI at 1/100 | 0.587 | 0.373 | 0.226 | 0.764 | 1.184 | 1.692 | 0.116 | 0.058 | 0.100 |
| DO15 at 1/100 | 1.613 | 0.859 | 1.286 | 3.357 | 3.693 | 3.038 | 0.673 | 0.036 | 0.075 |
| DJOU at 1/100 | 1.268 | 0.482 | 0.419 | 1.998 | 2.088 | 2.166 | 0.203 | 0.022 | 0.042 |
| 3600 at 1/100 | 0.482 | 0.360 | 0.249 | 0.716 | 0.801 | 0.933 | 0.206 | 0.025 | 0.058 |
| 3613 at 1/400 | 1.108 | 0.837 | 0.773 | 1.508 | 1.627 | 1.679 | 0.478 | 0.250 | 0.396 |
| 6111 at 1/100 | 0.596 | 0.348 | 0.202 | 0.850 | 1.207 | 1.009 | 0.226 | 0.087 | 0.180 |
| 625 at 1/50 | 0.838 | 0.338 | 0.264 | 2.045 | 2.122 | 1.791 | 0.202 | 0.069 | 0.165 |
| Maryland at 1/400 | 0.524 | 0.370 | 0.285 | 0.734 | 0.844 | 1.229 | 0.241 | 0.054 | 0.168 |
| 3653 at 1/10 | 0.347 | 0.337 | 0.247 | 0.072 | 0.380 | 0.406 | 0.401 | 0.021 | 0.310 |

SOLID PHASE*: PEPTIDE 2 μg/ml

For each peptide tested, the samples were arranged into four classes (a, b, c and d) corresponding to various levels of relative absorbance read at the wavelengths A492–A620:

for a: OD<0.100, for b: 0.100<OD<0.500, for c: 0.500<OD<1.000, for d: OD>1.000, thus making it possible to evaluate the degree of immunoreactivity of the peptides. The most immunoreactive peptides are those for which the highest number of samples is found in the classes corresponding to the highest absorbance values.

The results are indicated in Table VI.

TABLE VI

| | PEPTIDES* | | | | | | | | |
|---|---|---|---|---|---|---|---|---|---|
| CLASS | No. 10 | No. 11 | No. 12 | No. 14 | No. 15 | No. 16 | MVP 5180 | VAU 35 AA | VAU 22 AA |
| | Number of samples | | | | | | | | |
| A | 3 | 0 | 0 | 1 | 0 | 2 | 1 | 11 | 7 |
| B | 2 | 9 | 11 | 3 | 2 | 2 | 12 | 3 | 7 |
| C | 5 | 4 | 2 | 4 | 4 | 1 | 1 | 0 | 0 |
| D | 4 | 1 | 1 | 6 | 8 | 9 | 0 | 0 | 0 |

SOLID PHASE*: PEPTIDE 2 μg/ml

The results show that all the peptides of the invention tested achieve a better performance in immunoreactivity than the reference peptides of the prior art which are derived from natural isolates (MVP 5180, VAU). The peptides of the invention No. 15 (22B), No. 14 (21B), and No. 16 (23B) are found to be the most immunoreactive.

EXAMPLE 4

Evaluation of the Immunoreactivity of the Compositions Containing Peptides According to the Invention by an Immunoenzymatic test For this test, the procedure was carried out according to the protocol described in Example 2 and the same sera were used. The microplates used were sensitized either with peptide No. 1 (2B) cyclized, or with peptide No. 3 (4B) cyclized, or with a composition containing these two peptides (1:1 w/w). Into each well, there were deposited either 100 μl of a solution containing 2 μg/ml of peptide No. 1 (2B), or 100 μl of a solution containing 2 μg/ml of peptide No. 3 (4B), or 100 μl of a solution containing 1 μg/ml of peptide No. 1 (2B) and 1 μg/ml of peptide No. 3 (4B).

The results of this test are given in Table VII.

TABLE VII

| | ABSORBANCE | | |
|---|---|---|---|
| SERUM | PEPTIDE No. 1 (2B) (2 μg/ml) | PEPTIDE No. 3 (4B) (2 μg/ml) | PEPTIDE No. 1 (2B) (1 μg/ml) + PEPTIDE No. 3 (4B) (1 μg/ml) |
| 3529 | 1.503 | >* | > |
| 1105 | > | 1.421 | > |
| 3891 | 2.780 | > | > |
| 3235 | > | > | > |
| 2700 | > | > | > |
| 5931 | > | > | > |
| 3935 | 0.307 | > | > |
| 7443 | > | > | > |

TABLE VII-continued

| | ABSORBANCE | | |
|---|---|---|---|
| SERUM | PEPTIDE No. 1 (2B) (2 μg/ml) | PEPTIDE No. 3 (4B) (2 μg/ml) | PEPTIDE No. 1 (2B) (1 μg/ml) + PEPTIDE No. 3 (4B) (1 μg/ml) |
| 1062 | > | > | > |
| 1754 | > | > | > |
| 3136 | 0.302 | > | > |
| 6891 | 0.062 | > | > |
| 5149 | > | > | > |
| 5270 | > | > | > |
| 2551 | > | > | > |
| 3600 | 2.743 | > | > |
| 6976 | > | > | > |
| 4489 | > | > | > |
| 6165 | 2.714 | > | > |
| 6198 | > | > | > |
| 6627 | > | > | > |
| 6998 | > | > | > |
| 6697 | > | > | > |
| 7258 | 2.477 | > | > |
| 3627 | 2.910 | > | > |
| 4477* | > | > | > |
| 3771 | 0.544 | > | > |
| 1702 | 1.016 | > | > |
| 2294 | 0.447 | > | > |
| 2352 | 0.205 | > | > |
| 3016 | 0.243 | > | > |
| 3302 | 0.386 | > | > |
| 3482 | 1.473 | > | > |
| 3653 | 0.044 | 1.322 | 1.105 |
| 4364 | 1.382 | > | > |
| 3637 | > | > | > |
| 4288 | 2.802 | > | > |
| 5969 | > | > | > |
| 258 | > | > | > |
| 6111 | > | > | > |
| 625 | > | > | > |
| 6853 | > | 2.769 | > |
| 3136 | 0.302 | > | > |
| 6689 | > | 0.710 | > |
| 6295 | > | 1.718 | > |
| 4021 | > | 0.430 | 2.381 |
| 3884 | 1.839 | > | > |
| 6512 | > | 0.746 | > |
| 6487 | 2.687 | > | > |
| ESS | 2.494 | > | > |
| HAD | 0.041 | > | > |
| DUR | > | > | > |

*> = signal greater than the reading capacity of the spectrophotometer.

The results of Table VII demonstrate that the compositions of the peptides of the invention, when used in diagnosis, allow the detection of all the sera from patients infected with group O HIV-1 retroviruses.

What is claimed is:

1. Synthetic peptides in linear form, or cyclized by means of inter-cysteine disulphide bridges, having the general formula (I):

Δ-Z-Trp Gly Cys (residues 5 to 7 of SEQ ID NO: 1)-Θ-Cys Tyr Thr Ser (residues 13 to 16 of SEQ ID NO: 1)-Ω (I)

wherein:

Δ is selected from the group consisting of a biotinyl radical, a biocytinyl radical, a hydrogen atom, an acetyl ($CH_3CO$—) radical, an aliphatic chain which may contain one or two thiol, an aldehyde functional group and an amine functional group, Z is a peptide sequence selected from the group consisting of:

Leu Leu Ser Ser (residues 1 to 4 of SEQ ID NO: 3),
Leu Leu Asn Ser (residues 1 to 4 of SEQ ID NO: 6),
Arg Leu Asn Ser (residues 1 to 4 of SEQ ID NO: 16),
Ala Leu Glu Thr Leu Leu Gln Asn Gln Gln Leu Leu Asn Ser (residues 1 to 14 of SEQ ID NO: 11),
Ala Leu Glu Thr Leu Leu Gln Asn Gln Gln Leu Leu Asp Leu (residues 1 to 14 of SEQ ID NO: 13), Ala Leu Glu Thr Leu Leu Gln Asn Gln Gln Leu Leu Asn Ile (residues 1 to 14 of SEQ ID NO: 12), Leu Asn Gln Gln Arg Leu Leu Asn Ser (residues 1 to 9 of SEQ ID NO: 14), and Arg Ala Leu Glu Thr Leu Leu Asn Gln Gln Arg Leu Leu Asn Ser (residues 1 to 15 of SEQ ID NO: 15), Θ is a peptide sequence selected from the group consisting of:

Arg Gly Arg Leu Val (residues 8 to 12 of SEQ ID NO: 2),

Arg Gly Lys Leu Ile (SEQ ID NO: 17),

Arg Gly Lys Leu Val (SEQ ID NO: 18), and

Lys Gly Arg Leu Val (residues 8 to 12 of SEQ ID NO: 3),

Ω, attached to the —CO— group of Ser, is selected from the group consisting of:

a hydroxyl group and a peptide sequence of formula

Val-Ψ,

Val Arg Trp Asn Glu Thr-Ψ(residues 27–32 of SEQ ID NO: 11),

Val Gln Trp Asn Glu Thr-Ψ(residues 27 to 32 of SEQ ID NO: 1), and

Val Gln Trp Asn Ser Thr-Ψ(residues 27 to 32 of SEQ ID NO: 4), wherein Ψ, attached to the —CO— residue of Val or Thr, is selected from the group consisting of a OH group, a $NH_2$ group, and an alkoxy radical comprising from 1 to 6 carbon atoms.

2. Synthetic peptides of formula (I) according to claim 1 wherein Δ represents an aliphatic chain, said aliphatic chain being selected from the group consisting of an alkyl chain of 1 to 6 carbon atoms, an alkenyl chain of 2 to 6 carbon atoms, and an aminoalkylcabonyl chain of 2 to 6 carbon atoms.

3. Synthetic peptides of formula (I) according to claim 1 including one of the following sequences:

```
LLSLWGCRGRLVCYTSVQWNET or

Leu Leu Ser Leu Trp Gly Cys Arg Gly Arg Leu Val Cys Tyr Thr Ser Val Gln Trp Asn
 1              5                   10                  15                  20

Glu Thr (SEQ ID NO: 2),
    22

LLSSWGCKGRLVCYTSVQWNET or

Leu Leu Ser Ser Trp Gly Cys Lys Gly Arg Leu Val Cys Tyr Thr Ser Val Gln Trp Asn
 1              5                   10                  15                  20

Glu Thr (SEQ ID NO: 3),
    22

LLSSWGCKGRLVCYTSVQWNST or

Leu Leu Ser Ser Trp Gly Cys Lys Gly Arg Leu Val Cys Tyr Thr Ser Val Gln Trp Asn
 1              5                   10                  15                  20

Ser Thr (SEQ ID NO: 4),
    22

LLQSWGCKGRLVCYTSVQWNST or

Leu Leu Gln Ser Trp Gly Cys Lys Gly Arg Leu Val Cys Tyr Thr Ser Val Gln Trp Asn
 1              5                   10                  15                  20

Ser Thr (SEQ ID NO: 5),
    22

LLSSWGCRGRLVCYTSVQWNET or

Leu Leu Ser Ser Trp Gly Cys Arg Gly Arg Leu Val Cys Tyr Thr Ser Val Gln Trp Asn
 1              5                   10                  15                  20

Glu Thr (SEQ ID NO: 8),
    22

LLSSWGCKGRLVCYTS or

Leu Leu Ser Ser Trp Gly Cys Lys Gly Arg Leu Val Cys Tyr Thr Ser (SEQ ID NO: 9),
 1              5                   10                  15

LLNSWGCKGRLVCYTS or

Leu Leu Asn Ser Trp Gly Cys Lys Gly Arg Leu Val Cys Tyr Thr Ser (SEQ ID NO: 10),
 1              5                   10                  15

ALETLLQNQQLLNSWGCRGRLVCYTSVRWNET or

Ala Leu Glu Thr Leu Leu Gln Asn Gln Gln Leu Leu Asn Ser Trp Gly Cys Arg Gly
 1              5                   10                  15

Arg Leu Val Cys Tyr Thr Ser Val Arg Trp Asn Glu Thr (SEQ ID NO: 11),
```

-continued

```
 20                 25                  30

ALETLLQNQQLLNIWGCRGRLVCYTSVRWNET or

Ala Leu Glu Thr Leu Leu Gln Asn Gln Gln Leu Leu Asn Ile Trp Gly Cys Arg Gly
 1              5                   10                  15

Arg Leu Val Cys Tyr Thr Ser Val Arg Trp Asn Glu Thr (SEQ ID NO: 12),
 20                 25                  30

ALETLLQNQQLLDLWGCRGRLVCYTSVRWNET or

Ala Leu Glu Thr Leu Leu Gln Asn Gln Gln Leu Leu Asp Leu Trp Gly Cys Arg Gly
 1              5               10                  15

Arg Leu Val Cys Tyr Thr Ser Val Arg Trp Asn Glu Thr (SEQ ID NO: 13),
 20                 25                  30

LNQQRLLNSWGCKGRLVCYTSV or

Leu Asn Gln Gln Arg Leu Leu Asn Ser Trp Gly Cys Lys Gly Arg Leu Val Cys Tyr
 1              5                   10                  15

Thr Ser Val (SEQ ID NO: 14),
 20

RALETLLNQQRLLNSWGCKGRLVCYTSV or

Arg Ala Leu Glu Thr Leu Leu Asn Gln Gln Arg Leu Leu Asn Ser Trp Gly Cys Lys
 1              5                   10                  15

Gly Arg Leu Val Cys Tyr Thr Ser Val (SEQ ID NO: 15),
 20                 25

RLNSWGCKGRLVCYTSV or

Arg Leu Asn Ser Trp Gly Cys Lys Gly Arg Leu Val Cys Tyr Thr Ser Val (SEQ ID NO: 16).
 1              5                   10                  15
```

4. Composition containing at least one synthetic peptide of formula (I) according to claim 1, said peptide being freeze-dried or diluted in water.

5. Composition according to claim 4 containing, as the at least one synthetic peptide of formula (I), SEQ ID NO: 3 and SEQ ID NO: 1.

6. Composition containing at least one synthetic peptide of formula (I) according to claim 1 and at least one group O HIV-1 recombinant peptide.

7. Composition containing at least one synthetic peptide of formula (I) according to claim 1, and at least one HIV-1 and/or HIV-2 recombinant or synthetic peptide.

8. Immunoassay method for detecting a group O HIV-1 infection comprising the steps of a) obtaining a sample from a patient likely to contain anti-group O HIV-1 antibodies:
    b) contacting at least one synthetic peptide of formula (I) according to claim 1, detectably labeled, with said sample;
    c) detecting the presence or absence of a complex between said peptides and said antibodies;
    d) optionally assaying the amount of said antibodies in the sample; wherein the presence of a complex between said peptides and said antibodies is indicative of a group O HIV-1 infection.

9. Immunoassay method for detecting a group O HIV-1 infection comprising the steps of:

a) obtaining a sample from a patient likely to contain anti-group O HIV-1 antibodies;

b) contacting a composition according to claim 4, containing at least one synthetic peptide of formula (I), delectably labeled, with said sample:

c) detecting the presence or absence of a complex between said peptides and said antibodies; and d) optionally assaying the amount of said antibodies in the sample;

wherein the presence of a complex between said peptides and said antibodies is indicative of a group O HIV-1 infection.

10. Diagnostic kit for the detection of group O HIV-1 specific antibodies comprising a) a first container comprising at least one synthetic peptide of formula (I) according to claim 1 and b) second container comprising appropriate means of detection of complexes between said antibodies and said peptide.

11. Diagnostic kit for the detection of group O HIV-1 specific antibodies comprising a) first container comprising a composition according to claim 4 and b) a second container comprising appropriate means of detection of complexes between said antibodies and said peptide.

* * * * *

SEQUENCE LISTING

<160> NUMBER OF SEQ ID NOS: 22

<210> SEQ ID NO 1
<211> LENGTH: 22
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 1

Leu Leu Ser Leu Trp Gly Cys Arg Gly Lys Ala Val Cys Tyr Thr Ser
1 5 10 15

Val Gln Trp Asn Glu Thr
20

<210> SEQ ID NO 2
<211> LENGTH: 22
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 2

Leu Leu Ser Leu Trp Gly Cys Arg Gly Arg Leu Val Cys Tyr Thr Ser
1 5 10 15

Val Gln Trp Asn Glu Thr
20

<210> SEQ ID NO 3
<211> LENGTH: 22
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 3

Leu Leu Ser Ser Trp Gly Cys Lys Gly Arg Leu Val Cys Tyr Thr Ser
1 5 10 15

Val Gln Trp Asn Glu Thr
20

<210> SEQ ID NO 4
<211> LENGTH: 22
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 4

Leu Leu Ser Ser Trp Gly Cys Lys Gly Arg Leu Val Cys Tyr Thr Ser
1 5 10 15

Val Gln Trp Asn Ser Thr
20

<210> SEQ ID NO 5
<211> LENGTH: 22
<212> TYPE: PRT
<213> ORGANISM: Artificial Sequence
<220> FEATURE:
<223> OTHER INFORMATION: Description of Artificial Sequence: Synthetic peptide

<400> SEQUENCE: 5

Leu Leu Gln Ser Trp Gly Cys Lys Gly Arg Leu Val Cys Tyr Thr Ser
1 5 10 15

Val Gln Trp Asn Ser Thr
20

<210> SEQ ID NO 6
<211> LENGTH: 22
<212> TYPE: PRT
<213> ORGANISM: Artificial Sequence
<220> FEATURE:
<223> OTHER INFORMATION: Description of Artificial Sequence: Synthetic peptide

<400> SEQUENCE: 6

Leu Leu Asn Ser Trp Gly Cys Arg Gly Lys Ala Val Cys Tyr Thr Ser
1 5 10 15

Val Gln Trp Asn Glu Thr
20

<210> SEQ ID NO 7
<211> LENGTH: 22
<212> TYPE: PRT
<213> ORGANISM: Artificial Sequence
<220> FEATURE:
<223> OTHER INFORMATION: Description of Artificial Sequence: Synthetic peptide

<400> SEQUENCE: 7

Leu Leu Ser Leu Trp Gly Cys Arg Gly Arg Ala Val Cys Tyr Thr Ser
1 5 10 15

Val Gln Trp Asn Glu Thr
20

<210> SEQ ID NO 8
<211> LENGTH: 22
<212> TYPE: PRT
<213> ORGANISM: Artificial Sequence
<220> FEATURE:
<223> OTHER INFORMATION: Description of Artificial Sequence: Synthetic peptide

<400> SEQUENCE: 8

Leu Leu Ser Ser Trp Gly Cys Arg Gly Arg Leu Val Cys Tyr Thr Ser
1 5 10 15

Val Gln Trp Asn Glu Thr
20

<210> SEQ ID NO 9
<211> LENGTH: 16
<212> TYPE: PRT
<213> ORGANISM: Artificial Sequence
<220> FEATURE:
<223> OTHER INFORMATION: Description of Artificial Sequence: Synthetic peptide

<400> SEQUENCE: 9

Leu Leu Ser Ser Trp Gly Cys Lys Gly Arg Leu Val Cys Tyr Thr Ser
1 5 10 15

<210> SEQ ID NO 10
<211> LENGTH: 16
<212> TYPE: PRT

-continued

<213> ORGANISM: Artificial Sequence
<220> FEATURE:
<223> OTHER INFORMATION: Description of Artificial Sequence: Synthetic
peptide

<400> SEQUENCE: 10

Leu Leu Asn Ser Trp Gly Cys Lys Gly Arg Leu Val Cys Tyr Thr Ser
1 5 10 15

<210> SEQ ID NO 11
<211> LENGTH: 32
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 11

Ala Leu Glu Thr Leu Leu Gln Asn Gln Gln Leu Leu Asn Ser Trp Gly
1 5 10 15

Cys Arg Gly Arg Leu Val Cys Tyr Thr Ser Val Arg Trp Asn Glu Thr
20 25 30

<210> SEQ ID NO 12
<211> LENGTH: 32
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 12

Ala Leu Glu Thr Leu Leu Gln Asn Gln Gln Leu Leu Asn Ile Trp Gly
1 5 10 15

Cys Arg Gly Arg Leu Val Cys Tyr Thr Ser Val Arg Trp Asn Glu Thr
20 25 30

<210> SEQ ID NO 13
<211> LENGTH: 32
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 13

Ala Leu Glu Thr Leu Leu Gln Asn Gln Gln Leu Leu Asp Leu Trp Gly
1 5 10 15

Cys Arg Gly Arg Leu Val Cys Tyr Thr Ser Val Arg Trp Asn Glu Thr
20 25 30

<210> SEQ ID NO 14
<211> LENGTH: 22
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 14

Leu Asn Gln Gln Arg Leu Leu Asn Ser Trp Gly Cys Lys Gly Arg Leu
1 5 10 15

Val Cys Tyr Thr Ser Val
20

-continued

<210> SEQ ID NO 15
<211> LENGTH: 28
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 15

Arg Ala Leu Glu Thr Leu Leu Asn Gln Gln Arg Leu Leu Asn Ser Trp
1 5 10 15

Gly Cys Lys Gly Arg Leu Val Cys Tyr Thr Ser Val
20 25

<210> SEQ ID NO 16
<211> LENGTH: 17
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 16

Arg Leu Asn Ser Trp Gly Cys Lys Gly Arg Leu Val Cys Tyr Thr Ser
1 5 10 15

Val

<210> SEQ ID NO 17
<211> LENGTH: 5
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 17

Lys Gly Lys Leu Ile
1 5

<210> SEQ ID NO 18
<211> LENGTH: 5
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 18

Lys Gly Lys Leu Val
1 5

<210> SEQ ID NO 19
<211> LENGTH: 22
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 19

Leu Leu Asn Leu Trp Gly Cys Lys Asn Arg Ala Ile Cys Tyr Thr Ser
1 5 10 15

Val Lys Trp Asn Lys Thr
20

<210> SEQ ID NO 20

-continued

```
<211> LENGTH: 35
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Arg Leu Leu Ala Leu Glu Thr Phe Ile Glu Glu Asn Glu Leu Leu Asn
  1               5                  10                  15

Leu Trp Gly Cys Lys Asn Arg Ala Ile Cys Tyr Thr Ser Val Lys Trp
             20                  25                  30

Asn Lys Thr
         35


<210> SEQ ID NO 21
<211> LENGTH: 35
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Arg Leu Gln Ala Leu Glu Thr Leu Ile Gln Asn Gln Gln Arg Leu Asn
  1               5                  10                  15

Leu Trp Gly Cys Lys Gly Lys Leu Ile Cys Tyr Thr Ser Val Lys Trp
             20                  25                  30

Asn Thr Ser
         35


<210> SEQ ID NO 22
<211> LENGTH: 48
<212> TYPE: PRT
<213> ORGANISM: Artificial Sequence
<220> FEATURE:
<223> OTHER INFORMATION: Description of Artificial Sequence: synthetic
      peptide
<221> NAME/KEY: MOD_RES
<222> LOCATION: (29)
<223> OTHER INFORMATION: Cys or Ser
<221> NAME/KEY: MOD_RES
<222> LOCATION: (35)
<223> OTHER INFORMATION: Cys or Ser

<400> SEQUENCE: 22

Val Trp Gly Ile Arg Gln Leu Arg Ala Arg Leu Gln Ala Leu Glu Thr
  1               5                  10                  15

Leu Ile Gln Asn Gln Gln Arg Leu Asn Leu Trp Gly Xaa Lys Gly Lys
             20                  25                  30

Leu Ile Xaa Tyr Thr Ser Val Lys Trp Asn Thr Ser Trp Ser Gly Arg
         35                  40                  45
```